United States Patent [19]

Hirai et al.

[11] Patent Number: 5,319,134
[45] Date of Patent: Jun. 7, 1994

[54] PROCESS FOR INTRODUCING A CARBOXYL GROUP TO AN AROMATIC CARBOXYLIC ACID OR A DERIVATIVE THEREOF

[75] Inventors: Hidefumi Hirai, Tokyo; Rikinori Terakado, Yokohama; Hisashi Mihori, Tokyo; Tsutomu Nakamura, Yokohama; Kazuhiro Saito, Tokyo, all of Japan

[73] Assignee: Hidefumi Hirai, Tokyo, Japan

[21] Appl. No.: 966,448

[22] Filed: Oct. 26, 1992

[30] Foreign Application Priority Data

Oct. 25, 1991 [JP] Japan ................................. 3-305575

[51] Int. Cl.$^5$ ............................................. C07C 51/00
[52] U.S. Cl. .................................... 562/480; 562/490
[58] Field of Search ............... 562/480, 488, 490, 491, 562/492

[56] References Cited

U.S. PATENT DOCUMENTS 4,663,478  5/1987  Hirai et al. ........................... 562/475

FOREIGN PATENT DOCUMENTS 173748  3/1986  European Pat. Off. .

OTHER PUBLICATIONS

B. Raecke, Agnew. Chem., vol. 70, No. 1, pp. 1–5 (1958).
M. Komiyama et al, J. Am. Chem. Soc., vol. 105, No. 7, 2018–2021 (1983).
M. Komiyama et al., J. Am. Chem. Soc., vol. 106, No. 1, pp. 174–178 (1984).
M. Komiyama et al, J. Molecular Catalysis, 36 (1986) 271–282.
Chemical Abstracts, vol. 106, 1987, p. 8, left column, 106: 138873a.
Chemical Abstracts, vol. 112, 1990, p. 712, right column, 112: 55279j.
Y. Shiroto et al, Shokubai (Catalysts), vol. 33, No. 8, pp. 559–565 (1991).
Chemistry Letters, No. 8, Aug. 1992.

*Primary Examiner*—Arthur C. Prescott
*Attorney, Agent, or Firm*—Birch, Stewart, Kolasch & Birch

[57] ABSTRACT

Disclosed is a process for introducing a carboxyl group to an aromatic carboxylic acid or a derivative thereof, which comprises reacting a starting aromatic carboxylic acid, such as a benzoic acid, a biphenylcarboxylic acid, a naphthalenecarboxylic acid, a diphenylcarboxylic acid, or a derivative thereof, with a carbon tetrahalide in the presence of a cyclodextrin and an alkali metal hydroxide, thereby introducing a carboxyl group to the aromatic ring of the starting aromatic carboxylic acid or the derivative thereof in substitution for a hydrogen atom bonded thereto. By the process of the present invention, a desired aromatic polycarboxylic acid or a derivative thereof can be easily obtained with high selectivity.

13 Claims, No Drawings

PROCESS FOR INTRODUCING A CARBOXYL GROUP TO AN AROMATIC CARBOXYLIC ACID OR A DERIVATIVE THEREOF

BACKGROUND OF THE INVENTION

1. Field of the Invention

The present invention relates to a process for introducing a carboxyl group to an aromatic carboxylic acid or a derivative thereof. More particularly, the present invention is concerned with a process for introducing a carboxyl group to an aromatic carboxylic acid or a derivative thereof by reacting an aromatic carboxylic acid or a derivative thereof with a carbon tetrahalide in the presence of a cyclodextrin and an alkali metal hydroxide. By the process of the present invention, desired aromatic polycarboxylic acids or derivatives thereof can be easily obtained with high selectivity, which are commercially valuable raw materials for polyester films, resins and fibers; polyarylate films, resins and fibers; aramid films, resins and fibers; high molecular weight and low molecular weight compounds for various types of liquid crystals; agricultural chemicals; pharmaceuticals; and dyes.

2. Discussion of Related Art

For the production of aromatic polycarboxylic acids, known is a process which comprises oxidizing an aromatic hydrocarbon substituted with an alkyl group. However, this conventional process requires stringent conditions, for example, a high reaction temperature such as 160° C. or higher, a high reaction pressure such as 10 atm or higher, a large amount of a cobalt and a manganese catalyst, and a long residence time such as 20 hours or more. Further, this process is restricted in raw materials. For example, this process requires expensive raw materials, that is, paraxylene for producing terephthalic acid, metaxylene for producing isophthalic acid, 4,4'-dimethylbiphenyl for producing 4,4'-biphenyldicarboxylic acid, and 2,6-dimethylnaphthalene for producing 2,6-naphthalenedicarboxylic acid.

Also known is another process in which potassium benzoate is first produced from benzoic acid and then, the produced potassium benzoate is converted to dipotassium terephthalate and benzene by disproportionation. However, this process must also be conducted under stringent conditions, such as a temperature as high as 430° to 440° C., and a carbon dioxide pressure as high as 5 to 20 atm, using cadmium benzoate and zinc benzoate as catalysts. Therefore, it is difficult to control the reaction conditions and to handle the potassium salt.

In order to solve the problems accompanying the above-mentioned conventional processes for producing aromatic polycarboxylic acids, a technique in which a carboxyl group is directly introduced to an aromatic ring, has been proposed. For example, there are known the Kolbe-Schmitt reaction and the Reimer-Tiemann reaction, both of which are electrophilic aromatic substitution reactions. However, it is well known that those electrophilic aromatic substitution reactions have the following serious disadvantages: When either a hydroxyl group (—OH) or an amino group (—NH$_2$) is present as a substituent in an aromatic ring, the substitution reaction easily occurs at the ortho- or para-position relative to the hydroxyl group or the amino group, because the hydroxyl group or the amino group acts as a strong activating group in the electrophilic aromatic substitution reaction. On the other hand, when an aromatic ring contains either a carboxyl group or a carboxylic ester group as a substituent but contains neither a hydroxyl group nor an amino group as a substituent, either the carboxyl group or the carboxylic ester group acts as a strong deactivating group in the electrophilic aromatic substitution reaction, so that it is extremely difficult to directly introduce a carboxyl group to the aromatic carboxylic acid. In fact, there has been no report on the direct introduction of a carboxyl group to the aromatic carboxylic acid [see "Yuki Kagaku (I) (Organic Chemistry Vol I)", Third edition, p.428–431, written by Morrison-Boyd, translated by Nakanishi et al., and published by Tokyo Kagaku Dojin, Japan].

Further, when a hydroxyl group or an amino group is co-present with a carboxyl group in a starting aromatic carboxylic acid, a carboxyl group to be introduced to such a starting aromatic carboxylic acid exhibits a substitution orientation for the ortho- or para-position relative to the hydroxyl group or the amino group, due to the strong activity of the hydroxyl or the amino group in the electrophilic aromatic substitution reaction. Therefore, it is impossible to obtain from such a starting aromatic carboxylic acid an aromatic polycarboxylic acid having a carboxyl group additionally introduced to an aromatic ring thereof at a position remote from the meta-position relative to the carboxyl group which is originally attached to the starting aromatic carboxylic acid.

SUMMARY OF THE INVENTION

In these situations, the present inventors have made extensive and intensive studies with a view toward developing a new process for the direct introduction of a carboxyl group to an aromatic carboxylic acid or a derivative thereof. As a result, it has surprisingly been found that when an aromatic carboxylic acid or a derivative thereof is reacted with a carbon tetrahalide in the presence of a cyclodextrin and an alkali metal hydroxide, even if the aromatic carboxylic acid or the derivative thereof has neither a hydroxyl group nor an amino group as a substituent, a direct introduction of a carboxyl group to the aromatic carboxylic acid or the derivative thereof can be effectively and efficiently performed under mild conditions. Furthermore, it has been found that even when a starting aromatic carboxylic acid or a derivative thereof has either a hydroxyl group or an amino group as a substituent, by reacting the starting aromatic carboxylic acid or the derivative thereof with a carbon tetrahalide in the presence of a cyclodextrin and an alkali metal hydroxide, a carboxyl group can be introduced to a position other than the ortho- or para-position relative to the hydroxyl group or the amino group. That is, when the starting aromatic carboxylic acid or the derivative thereof is a monocarboxylic acid or a derivative thereof, a carboxyl group can be introduced to a position remote from the meta-position relative to the carboxyl group originally attached to the starting aromatic monocarboxylic acid or the derivative thereof unless a substituent group is present at the above-mentioned position to be substituted with a carboxyl group in the monocarboxylic acid, and when the starting aromatic carboxylic acid or the derivative thereof is a polycarboxylic acid or a derivative thereof, a carboxyl group can be introduced to a position remote from the meta-position relative to the respective carboxyl group originally attached to the starting aromatic polycarboxylic acid or the derivative thereof unless a substituent group is present at the above-mentioned position to be substituted with a carboxyl group in the polycarboxylic acid. This is unexpected from the inherent meta-substitution orientation of a carboxyl group relative to the carboxyl group of the starting aromatic carboxylic acid [see, for example, "Yuki Kagaku (II) (Organic Chemistry Vol II)", Fifth edition, p. 645–653 written by Morrison-Boyd, translated by Nakanishi et al., and published by Tokyo Kagaku Dojin, Japan]. That is, the effect of the present invention is quite surprising from the strong activity of a carboxyl group as a substituent of an aromatic ring to deactivate the electrophilic aromatic substitution reaction and the strong activity of a substituent hydroxyl group or a substituent amino group. The present invention has been made, based on these novel findings.

It is, therefore, an object of the present invention to provide a process for introducing a carboxyl group to an aromatic carboxylic acid or a derivative thereof, which process is free from the drawbacks inevitably accompanying the conventional processes and is suitable for producing various types of aromatic polycarboxylic acids or derivatives thereof with high selectivity.

The foregoing and other objects, features and advantages have been achieved according to the present invention and will be apparent to those skilled in the art from the following detailed description and appended claims.

DETAILED DESCRIPTION OF THE INVENTION

According to the present invention, there is provided a process for introducing a carboxyl group to an aromatic carboxylic acid or a derivative thereof, which comprises reacting an aromatic carboxylic acid or a derivative thereof represented by formula (1), (2), (3) or (4) with a carbon tetrahalide in the presence of a cyclodextrin and an alkali metal hydroxide, thereby introducing a carboxyl group to the aromatic carboxylic acid or the derivative thereof in substitution for a hydrogen atom which is bonded to an aromatic ring of the aromatic carboxylic acid or the derivative thereof, wherein, formula (1) is:

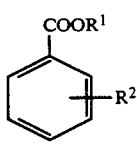

wherein:
$R^1$ is a hydrogen atom, an alkyl group or an alkali metal, and
$R^2$ is a hydrogen atom, an alkyl group, an alkoxyl group, a carboxyl group, a nitro group or a halogen atom, bonded to the ortho- or meta-position relative to COOR$^1$, formula (2) is:

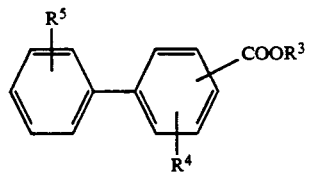

wherein:
$R^3$ is a hydrogen atom, an alkyl group or an alkali metal,
$R^4$ is a hydrogen atom, an alkyl group, an alkoxyl group, a carboxyl group, a nitro group, an amino group or a halogen atom,
COOR$^3$ is bonded to the 2-, 3- or 4-position, in which,
$R^4$ is bonded to the 3-, 4-, 5- or 6-position when COOR$^3$ is bonded to the 2-position, bonded to the 2-, 4-, 5- or 6-position when COOR$^3$ is bonded to the 3-position, and bonded to the 2- or 3-position when COOR$^3$ is bonded to the 4-position, and
$R^5$ is a hydrogen atom, a hydroxyl group, an alkyl group, an alkoxyl group, a carbonyl group, a nitro group, an amino group or a halogen atom, bonded to the 2'-, 3'-, 4'-, 5'- or 6'-position, formula (3) is:

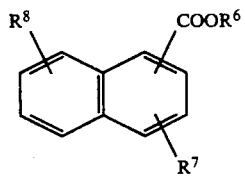

wherein:
$R^6$ is a hydrogen atom, an alkyl group or an alkali metal,
$R^7$ is a hydrogen atom, a hydroxyl group, an alkyl group, an alkoxyl group, a carboxyl group, a nitro group, an amino group or a halogen atom,
COOR$^6$ is bonded to the 1- or 2-position, in which,
$R^7$ is bonded to the 2-, 3-, or 4-position when COOR$^6$ is bonded to the 1-position, and bonded to the 1-, 3- or 4-position when COOR$^6$ is bonded to the 2-position, and
$R^8$ is a hydrogen atom, a hydroxyl group, an alkyl group, an alkoxyl group, a carboxyl group, a nitro group, an amino group or a halogen atom, bonded to the 5-, 6-, 7-, or 8-position, and formula (4) is:

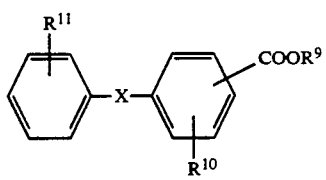

wherein:
$R^9$ is a hydrogen atom, an alkyl group or an alkali metal,
$R^{10}$ is a hydrogen atom, a hydroxyl group, an alkyl group, an alkoxyl group, a carboxyl group, a nitro group, an amino group or a halogen atom,
COOR$^9$ is bonded to the 2-, 3- or 4-position, in which, $R^{10}$ is bonded to the 3-, 4-, 5- or 6-position when $COOR^9$ is bonded to the 2-position, bonded to the 2-, 4-, 5- or 6-position when $COOR^9$ is bonded to the 3-position, and bonded to the 2- or 3-position when $COOR^9$ is bonded to the 4-position, $R^{11}$ is a hydrogen atom, a hydroxyl group, an alkyl group, an alkoxyl group, a carboxyl group, a nitro group, an amino group or a halogen atom, bonded to the 2'-, 3'-, 4'-, 5'- or 6'-position, and X is —O—, —CH$_2$—, —C(CH$_3$)$_2$—, —CH=CH—, —(C=O)—, —NH—, —N=N—, —S— or —SO$_2$—.

In the present invention, the identification of a substitution position of a chemical compound is made in accordance with the nomenclature of IUPAC.

A starting material to be used in the process of the present invention is selected from the group consisting of benzoic acid or a derivative thereof represented by formula (1) (hereinafter, frequently referred to simply as "a benzoic acid"), biphenylcarboxylic acid or a derivative thereof represented by formula (2) (hereinafter, frequently referred to simply as "a biphenylcarboxylic acid"), naphthalenecarboxylic acid or a derivative thereof represented by formula (3) (hereinafter, frequently referred to simply as "a naphthalenecarboxylic acid"), and diphenylcarboxylic acid or a derivative thereof represented by formula (4) (hereinafter, frequently referred to simply as "a diphenylcarboxylic acid").

Examples of alkyl groups and examples of alkyl moieties of alkoxyl groups, which groups are represented by $R^1$, $R^2$ and $R^3$, $R^4$, $R^5$, $R^6$, $R^7$, $R^8$, $R^9$, $R^{10}$, and $R^{11}$ of formulae (1)–(4), include straight chain or branched chain hydrocarbon residues having 1 to 12 carbon atoms, and examples of halogen atoms represented by $R^2$ and $R^3$, $R^4$, $R^5$, $R^7$, $R^8$, $R^{10}$, and $R^{11}$ include F, Cl, Br and I, preferably Cl and Br.

As a cyclodextrin to be used in the process of the present invention, there can be mentioned β-cyclodextrin and γ-cyclodextrin. Of these, β-cyclodextrin is most preferred. Further, a cyclodextrin modified with a methyl group, an ethyl group, a hydroxyethyl group or a hydroxypropyl group can also be used. A solid, fixed cycrodextrin produced by crosslinking the hydroxyl groups of the above-mentioned cyclodextrin with a hydroxyalkyl group can also be used in the process of the present invention. The use of a solid, fixed cyclodextrin is advantageous in that expensive cyclodextrin can be recovered and used repeatedly. With respect to the details of the solid, fixed cyclodextrin, reference can be made to the specification of U.S. Pat. No. 4,663,478.

In the process of the present invention, a cyclodxtrin may generally be used in an amount of 0.01 to 5 in terms of the molar ratio relative to an aromatic carboxylic acid as a starting material. Preferably, molar ratios of a cyclodextrin are 0.1 to 2 relative to a benzoic acid, and 0.2 to 2 relative to a biphenylcarboxylic acid, a naphthalenecarboxylic acid or a diphenylcarboxylic acid. On the other hand, a molar ratio of a cyclodextrin to a carbon tetrahalide is preferably 0.001 to 3.

As examples of carbon tetrahalides to be used in the present invention, there can be mentioned carbon tetrachloride and carbon tetrabromide. Carbon tetrahalide may be used in an amount of 1 to 200 in terms of the molar ratio relative to an aromatic carboxylic acid as a starting material. Preferably, molar ratios of a carbon tetrahalide are 1 to 100 relative to a benzoic acid, 1 to 100 relative to a biphenylcarboxylic acid, and 1 to 20 relative to a naphthalenecarboxylic acid or a diphenylcarboxylic acid.

As examples of alkali metal hydroxides used in the present invention, there can be mentioned sodium hydroxide and potassium hydroxide. The alkali metal hydroxide is generally used in an amount of 3 to 130, preferably 20 to 100 in terms of the molar ratio relative to an aromatic carboxylic acid as a starting material. As mentioned below, the process of the present invention is usually performed in a reaction medium. The alkali metal hydroxide is usually employed in the form of a solution thereof in the reaction medium in a concentration of from 1 to 50% by weight, preferably from 10 to 35% by weight.

As mentioned above, the process of the present invention is usually carried out in a reaction medium. As a reaction medium, there is employed an aqueous solvent, preferably water, because it is required that the reaction medium be capable of dissolving the alkali metal hydroxide therein. There may also be used, as the reaction medium, a mixture of water with a small amount of an organic solvent which is soluble in water and can be present stably under the reaction conditions. Examples of such an organic solvent include methanol, ethanol, acetone and dimethoxyethane. The reaction medium is usually employed in an amount of from 50 to 1000 moles, preferably from 300 to 600 moles per mole of the starting aromatic carboxylic acid.

The process of the present invention can be conducted without a copper catalyst. However, in the presence of a copper catalyst, the reaction can more smoothly proceed as compared to the reaction without a copper catalyst. As a copper catalyst, there can be mentioned, for example, powdery copper, copper bronze (e.g., reference may be made to Aldrich Catalog Handbook of Fine Chemicals 1990–1991, p. 345, U.S.A.), copper chromite, copper(I) oxide, copper sulfate and copper(I) acetylacetonato. With respect to powdery copper and copper bronze, small particles having an average particle diameter of from 0.5 to 300 μm are preferred. In general, a copper catalyst may be used in an amount of from 0.01 to 4 in terms of the molar ratio of copper atom relative to an aromatic carboxylic acid as a starting material. When a copper catalyst is powdery copper, copper (I) oxide or copper sulfate, a preferred amount of the copper catalyst is 0.3 to 2 in terms of the molar ratio of copper atom to the aromatic carboxylic acid as a starting material, and when a copper catalyst is copper bronze, copper chromite or copper (I) acetylacetonato, a preferred amount of the copper catalyst is 0.01 to 0.5 in terms of the molar ratio of copper atom to the aromatic carboxylic acid as a starting material.

The reaction temperature is generally 20° to 85° C., preferably 40° to 70° C.

The reaction time is not specifically restricted but generally is 5 minutes to 40 hours. The reaction time may be varied depending on the types and amounts of the aromatic carboxylic acid, carbon tetrahalide, cyclodextrin and copper catalyst, the reaction temperature, the manner for the addition of a starting material and a reactant, and the like.

The reaction may be carried out in air, but preferably in a nitrogen atmosphere. The reaction pressure is also not specifically restricted, but, from a viewpoint of ease in operation, the reaction may be usually performed at an atmospheric pressure.

When the process of the present invention is practiced, all the amount of the carbon tetrahalide may be added to a reaction system comprising an aromatic carboxylic acid, an alkali metal hydroxide and a cyclodextrin at the time of initiation of the reaction. Alternatively, as shown in Example 29 described later, a carbon tetrahalide may be gradually added to the above-mentioned reaction system so that the molar ratio of the cyclodextrin to the carbon tetrahalide is maintained at 0.001 to 3.

In the reaction involved in the process of the present invention, a cyclodextrin acts as a catalyst and provides a special effective field for the reaction. Actually, the reaction does substantially not proceed in the absence of a cyclodextrin. With respect to the use of a cyclodextrin, the following effects are noted. A carbon tetrahalide is hardly dissolved in an alkaline aqueous solution as a reaction medium, but can be dissolved in the alkaline aqueous solution in the presence of a cyclodextrin. Further, a cyclodextrin is effective not only for improving the solubility of a carbon tetrahalide in an alkaline aqueous solution as a reaction medium, but also for introducing a carboxyl group to an aromatic ring of a starting aromatic carboxylic acid at a position remote from the meta-position relative to the carboxyl group which is originally attached to the starting aromatic carboxylic acid, thereby obtaining a desired aromatic polycarboxylic acid in high yield with high selectivity. This is surprising from the fact that even though a large amount of ethanol, which is effective for improving the solubility of a carbon tetrahalide in an alkaline aqueous solution, is used in place of a cyclodextrin, there cannot be obtained a desired aromatic polycarboxylic acid having a carboxyl group introduced to the aromatic ring at a position remote from the meta-position relative to the carboxyl group which is originally attached to the starting aromatic carboxylic acid, but there is formed an aromatic polycarboxylic acid having a carboxyl group introduced to the meta-position relative to the carboxyl group of the starting carboxylic acid (see, for example, Comparative Example 2 described later).

In the process of the present invention, when an aromatic carboxylic acid or a derivative thereof represented by formula (1) is used as a starting material, a terephthalic acid or a derivative thereof represented by the following formula (5) can be selectively obtained:

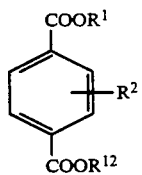

(5)

wherein $R^1$ and $R^2$ are as defined for formula (1) and $R^{12}$ is a hydrogen atom or an alkali metal.

Examples of terephthalic acids and derivatives thereof include terephthalic acid, methylterephthalic acid, methoxyterephthalic acid, 1,2,4-benezenetricarboxylic acid, nitroterephthalic acid, chloroterephthalic acid and sodium salts thereof. These terephthalic acid and derivatives thereof are commercially valuable raw materials for polyester fibers, films and resins; aramid fibers, films and resins; polyarylate fibers, films and resins; high molecular weight and low molecular weight compounds for liquid crystals; agricultural chemicals; pharmaceuticals; and dyes.

In the process of the present invention, when a biphenylcarboxylic acid or a derivative thereof represented by formula (2) is used as a starting material, a biphenyldicarboxylic acid or a derivative thereof represented by the following formula (6) can be selectively obtained:

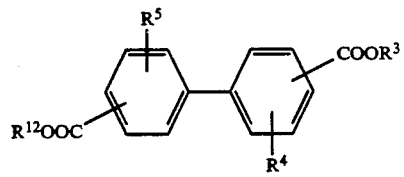

(6)

wherein $R^3$, $R^4$ and $R^5$ are as defined for formula (2) and $R^{12}$ is as defined for formula (5), and wherein $COOR^{12}$ is bonded to the 2'-, 3'-, 4'-, 5'- or 6'-position, exclusive of the position of $R^5$ of the starting material when $R^5$ is a substituent other than a hydrogen atom.

Examples of biphenyldicarboxylic acids and derivatives thereof include 4,4'-biphenyldicarboxylic acid, 2,2'-biphenyldicarboxylic acid, 3,3'-biphenyldicarboxylic acid, 2,4'-biphenyldicarboxylic acid, 3-methyl-4,4'-biphenyldicarboxylic acid, 3-methoxy-4,4'-biphenyldicarboxylic acid, 3,4,4'-biphenyltricarboxylic acid, 3-nitro-4,4'-biphenyldicarboxylic acid, 2-chloro-4,4'-biphenyldicarboxylic acid, 4-amino-3,4'-biphenyldicarboxylic acid and sodium salts thereof. These biphenyldicarboxylic acids and derivatives thereof are commercially valuable raw materials for polyester fibers, films and resins; aramid fibers, films and resins; polyarylate fibers, films and resins; high molecular weight and low molecular weight compounds for liquid crystals; and the like.

In the process of the present invention, when a naphthalenecarboxylic acid or a derivative thereof represented by formula (3) is used as a starting material, a naphthalenedicarboxylic acid or a derivative thereof represented by the following formula (7) can be selectively obtained:

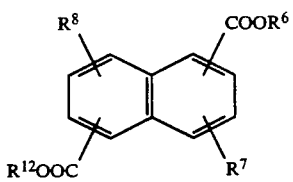

(7)

wherein $R^6$, $R^7$ and $R^8$ are as defined for formula (3) and $R^{12}$ is as defined for formula (5), and wherein $COOR^{12}$ is bonded to the 5-, 6-, 7- or 8-position, exclusive of the position of $R^8$ of the starting material when $R^8$ is a substituent other than a hydrogen atom.

Examples of naphthalenedicarboxylic acids and derivatives thereof include 2,6-naphthalenedicarboxylic acid, 2,7-naphthalenedicarboxylic acid, 1,6-naphthalenedicarboxylic acid, 3-hydroxy-2,6-naphthalenedicarboxylic acid, 8-methyl-2,6-naphthalenedicarboxylic acid, 8-methoxy-2,6-naphthalenedicarboxylic acid, 1,2,6-naphthalenetricarboxylic acid, 8-nitro-2,6-naphthalenedicarboxylic acid, 7-amino-2,6-naphthalenedicarboxylic acid, 7-bromo-2,6-naphthalenedicarboxylic acid and sodium salts thereof.

These naphthalenedicarboxylic acids and derivatives thereof are commercially valuable raw materials for polyester fibers, films and resins; polyarylate fibers, films and resins; high molecular weight and low molecular weight compounds for liquid crystals; dyes; and the like.

In the process of the present invention, when a diphenylcarboxylic acid or a derivative thereof represented by formula (4) is used as a starting material, a diphenyldicarboxylic acid or a derivative thereof represented by the following formula (8) can be selectively obtained:

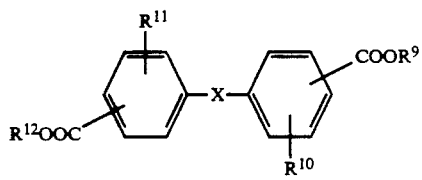

(8)

wherein $R^9$, $R^{10}$ and $R^{11}$ are as defined for formula (4) and $R^{12}$ is as defined for formula (5), and wherein $COOR^{12}$ is bonded to the 2'-, 3'-, 4'-, 5'- or 6'-position, exclusive of the position of $R^3$ of a starting material when $R^{11}$ is a substituent other than a hydrogen atom.

Examples of diphenyldicarboxylic acids and derivatives thereof include 4,4'-dicarboxy-diphenyl ether, 4-(4'-carboxybenzoyl) benzoic acid, 4-(4'-carboxyphenyldimethylmethyl) benzoic acid, 4-(4'-carboxystyryl) benzoic acid, 4-(4'-carboxybenzoyl) benzoic acid, 4,4'-iminodibenzoic acid, 4,4'-(1,1'-azo) benzoic acid, 4,4'-thiodibenzoic acid, 4,4'-sulfonyldibenzoic acid and sodium salts thereof. These diphenyldicarboxylic acids and derivatives thereof are commercially valuable raw materials for polyester fibers, films and resins; polyarylate fibers, films and resins; high molecular weight and low molecular weight compounds for liquid crystals; agricultural chemicals; pharmaceuticals; dyes; and the like.

The desired aromatic polycarboxylic acid obtained according to the process of the present invention can be isolated as follows. When a reaction mixture obtained by the reaction for introducing a carboxyl group to an aromatic carboxylic acid or a derivative thereof is neutralized and weakly acidified to pH 2 to 5, the desired aromatic polycarboxylic acid and most of an unreacted starting aromatic carboxylic acid are caused to precipitate. The precipitates are obtained as a filter cake by filtration. The unreacted starting aromatic carboxylic acid and by-products contained in the filter cake are soluble in methanol or ethanol in the pH range of from 2 to 5, whereas the desired aromatic polycarboxylic acid is insoluble therein. Therefore, the desired aromatic polycarboxylic acid can be separated from the unreacted starting aromatic carboxylic acid and by-products by subjecting the filter cake to extraction with methanol or ethanol and removing the methanol- or ethanol-extracted, unreacted starting aromatic carboxylic acid and by-products.

Alternatively, when production of a desired aromatic polycarboxylic acid of high purity is intended, an ion exchange column chromatography can be used. As the ion exchange column, a strong anion exchange column is preferred. When purification is conducted using a strong anion exchange column, the above-mentioned alcohol-treated filter cake is added to a solution obtained by adding acetonitrile to an aqueous solution of sodium nitrate and boric acid (the pH value of which aqueous solution has been adjusted to 9.7 with sodium hydroxide), and stirred to thereby dissolve the reaction products therein, followed by filtration. Then, the filtrate is applied to the strong anion exchange column. When a monocarboxylic acid is used as a starting material, the desired dicarboxylic acid is eluted earlier than the unreacted monocarboxylic acid, so that the dicarboxylic acid can be isolated from the unreacted monocarboxylic acid. Likewise, when a dicarboxylic acid is used as a starting material, the desired tricarboxylic acid is eluted earlier than the unreacted dicarboxylic acid, so that the tricarboxylic acid can be isolated from the unreacted dicarboxylic acid. Undesired by-products can also be removed utilizing the difference in the order of elution in the chromatography. In the above operation, when the desired aromatic polycarboxylic acid is a terephthalic acid, the acetonitrile content of the above-mentioned solution for treating the filter cake is preferably 0 to 5 vol %. When the desired aromatic polycarboxylic acid is a biphenyldicarboxylic acid, a naphthalenedicarboxylic acid or a diphenyldicarboxylic acid, the acetonitrile content of the above-mentioned solution is preferably 10 to 25 vol %.

As described above, according to the process of the present invention, the introduction of a carboxyl group to an aromatic carboxylic acid can be easily performed even if the aromatic carboxylic acid has neither a hydroxyl group nor an amino group. Further, according to the present invention, when a starting aromatic carboxylic acid has either a hydroxyl group or an amino group, the carboxyl group can be introduced into a position which is not the ortho- or para-position relative to the position of the hydroxyl group or the amino group, but remote from the meta-position relative to the carboxyl group originally attached to the starting aromatic carboxylic acid, which is quite unexpected from the fact that a carboxyl group inherently has a meta-orientation relative to the carboxyl group originally attached to the starting aromatic carboxylic acid. Accordingly, by virtue of the present invention, it has become possible to obtain a useful aromatic polycarboxylic acid. For example, according to the present invention, aromatic dicarboxylic acids which are commercially valuable raw materials for, for example, many types of high performance resins, fibers, and high molecular weight and low molecular weight compounds for liquid crystals, can be effectively obtained from an aromatic monocarboxylic acid, such as benzoic acid or a derivative thereof, with high selectivity. Furthermore, it should be noted that according to the process of the present invention, a desired aromatic polycarboxylic acid can be obtained with high selectivity by stepwise introducing additional carboxyl group one by one to an aromatic carboxylic acid.

PREFERRED EMBODIMENT OF THE INVENTION

The present invention will be illustrated in more detail with reference to the following Examples, but should not be construed as limiting the scope of the invention.

In the following Examples, analysis of a starting material and a reaction product is performed by liquid chromatography, in which a high performance liquid chromatography (HPLC) apparatus (8010 series HPLC, manufactured and sold by Tosoh Corp., Japan)

equipped with an ultraviolet-visible absorption spectrophotometer (UV-8010, manufactured and sold by Tosoh Corp., Japan) and an ion exchange column (TSK-gel SAX, strong anion exchange column, manufactured and sold by Tosoh Corp., Japan) is used.

In the case of the reaction using benzoic acid represented by formula (1) as a starting material, analysis is performed using a developing solution containing 0.3M sodium nitrate, 0.05M boric acid (pH: 9.7) and 5 vol % acetonitrile, under the following conditions: a detective wavelength of 254 nm, a flow rate of 1.0 ml/min., and a column temperature of 40° C. However, when an isophthatic acid is analyzed, a developing solution containing 0.3M sodium nitrate and 0.05M boric acid (pH: 9.7) is used instead of the above-mentioned developing solution. In the case of the reaction using any of other carboxylic acids represented by formulae (2) to (4) as a starting material, analysis is performed using a developing solution containing 0.5M sodium nitrate, 0.05M boric acid (pH: 9.8) and 10–25 vol % acetonitrile, under the following conditions: a detective wavelength of 258 nm, a flow rate of 1.0 ml/min., and a column temperature of 40° C. After completion of the reaction, a qualitative determination is performed by comparing individual retention times of the remaining starting material and the reaction product with those of standard substances individually corresponding thereto. A quantitative determination is performed according to the absolute calibration curve method. The yield of a reaction product is indicated in terms of mol % relative to the aromatic carboxylic acid used as the starting material. The amount of the unreacted starting aromatic carboxylic acid remaining in a reaction mixture is indicated in terms of mol % relative to the aromatic carboxylic acid used as the starting material.

EXAMPLE 1

In a 200 ml round bottom flask provided with a reflux condenser are placed 0.36 g (3.00 mmol) of benzoic acid (special grade reagent, manufactured and sold by Kanto Chemical Co., Ltd., Japan), 0.05 g (0.80 mmol) of powdery copper (first class grade reagent, manufactured and sold by Kanto Chemical Co., Ltd., Japan), and 1.7 g (1.50 mmol) of $\beta$-cyclodextrin (manufactured and sold by Tokyo Kasei Co., Ltd., Japan). After replacing the air in the flask with a nitrogen gas, 30 ml of an aqueous 30 wt % sodium hydroxide solution is added and agitated well by means of a magnetic stirrer, followed by heating to 60° C. 0.9 ml (9.55 mmol) of carbon tetrachloride (special grade reagent, manufactured and sold by Kanto Chemical Co., Ltd., Japan) is added thereto and a reaction is allowed to proceed for 7 hours. Then, the obtained mixture is cooled and then, neutralized and acidified to pH 2 with hydrochloric acid, to thereby terminate the reaction. The reaction mixture is subjected to filtration. The obtained filtrate is neutralized with an aqueous sodium hydrogencarbonate solution (first class grade reagent, manufactured and sold by Kanto Chemical Co., Ltd., Japan) and then qualitatively and quantitatively analyzed with respect to the remaining starting material and the reaction product by the above-mentioned liquid chromatography. On the other hand, the filter cake is added to 200 ml of 0.5M sodium hydrogencarbonate solution and stirred for 3 hours to thereby dissolve the remaining starting material and the reaction product therein. The resultant solution is subjected to filtration. The obtained filtrate is qualitatively and quantitatively analyzed by liquid chromatography. As a result of the analysis, it is found that terephthalic acid and isophthalic acid are obtained in yields of 31.0 mol % and 1.8 mol %, respectively, and phthalic acid is not detected. It is also found that the amount of unreacted benzoic acid is 37.0 mol %.

EXAMPLE 2

Substantially the same procedure as in Example 1 is repeated except that 0.35 g (0.31 mmol) of $\beta$-cyclodextrin is used instead of 1.7 g (1.50 mmol) of $\beta$-cyclodextrin. As a result of the analysis of the reaction mixture, it is found that only terephthalic acid is obtained in a yield of 9.9 mol % and neither phthalic acid nor isophthalic acid is detected. It is also found that the amount of unreacted benzoic acid is 86.0 mol %.

EXAMPLE 3

Substantially the same procedure as in Example 1 is repeated except that 6.8 g (6.00 mmol) of $\beta$-cyclodextrin is used instead of 1.7 g (1.50 mmol) of $\beta$-cyclodextrin. As a result of the analysis of the reaction mixture, it is found that terephthalic acid and isophthalic acid are obtained in yields of 7.0 mol % and 3.3 mol %, respectively, and phthalic acid is not detected. It is also found that the amount of unreacted benzoic acid is 58.1 mol %.

EXAMPLE 4

Substantially the same procedure as in Example 1 is repeated except that 6.0 ml (62.4 mmol) of carbon tetrachloride is used instead of 0.9 ml (9.55 mmol) of carbon tetrachloride. As a result of the analysis of the reaction mixture, it is found that terephthalic acid and isophthalic acid are obtained in yields of 44.4 mol % and 5.0 mol %, respectively, and phthalic acid is not detected. It is also found that the amount of unreacted benzoic acid is 25.7 mol %.

COMPARATIVE EXAMPLE 1

Substantially the same procedure as in Example 1 is repeated except that $\beta$-cyclodextrin is not used. As a result of the analysis of the reaction mixture, it is found that the reaction has substantially not proceeded.

COMPARATIVE EXAMPLE 2

Substantially the same procedure as in Example 1 is repeated except that a mixed solvent of an aqueous 30 wt % sodium hydroxide solution and ethanol (1:2) is used instead of 30 ml of an aqueous 30 wt % sodium hydroxide solution and $\beta$-cyclodextrin is not used. As a result of the analysis of the reaction mixture, it is found that isophthalic acid is obtained in a yield of 1.1 mol %. It is also found that the amount of unreacted benzoic acid is 98.9 mol %.

EXAMPLE 5

In substantially the same reaction apparatus as employed in Example 1 are placed 0.36 g (3.00 mmol) of benzoic acid, 0.05 g (0.80 mmol) of powdery copper and 1.7 g (1.50 mmol) of $\beta$-cyclodextrin. After replacing the air in the flask with a nitrogen gas, 30 ml of an aqueous 15 wt % sodium hydroxide solution is added and agitated well by means of a magnetic stirrer, followed by heating to 60° C. 0.9 ml (9.55 mmol) of carbon tetrachloride is added thereto and a reaction is allowed to proceed for 7 hours. Then, the obtained mixture is cooled and then, neutralized and acidified to pH 2 with hydrochloric acid, to thereby terminate the reaction. As a result of the analysis of the reaction mixture, it is found that terephthalic acid and isophthalic acid are obtained in yields of 7.3 mol % and 1.3 mol %, respectively, and phthalic acid is not detected. It is also found that the amount of unreacted benzoic acid is 87.2 mol %.

COMPARATIVE EXAMPLE 3

Substantially the same procedure as in Example 5 is repeated except that $\beta$-cyclodextrin is not used. As a result of the analysis of the reaction mixture, it is found that only terephthalic acid is obtained in a yield of 0.1 mol % and neither phthalic acid nor isophthalic acid is detected. It is also found that the amount of unreacted benzoic acid is 98.7 mol %.

EXAMPLE 6

Substantially the same procedure as in Example 5 is repeated except that 30 ml of an aqueous 40 wt % sodium hydroxide solution is used instead of 30 ml of the aqueous 15 wt % sodium hydroxide solution. As a result of the analysis of the reaction mixture, it is found that only terephthalic acid is obtained in a yield of 0.5 mol % and neither phthalic acid nor isophthalic acid is detected. It is also found that the amount of unreacted benzoic acid is 96.4 mol %.

EXAMPLE 7

Substantially the same procedure as in Example 1 is repeated except that 1.9 g (1.46 mmol) of $\gamma$-cyclodextrin (special grade reagent, manufactured and sold by Nacalai Tesque, Japan) is used instead of $\beta$-cyclodextrin. As a result of the analysis of the reaction mixture, it is found that terephthalic acid and isophthalic acid are obtained in yields of 2.8 mol % and 2.5 mol %, respectively, and phthalic acid is not detected. It is also found that the amount of unreacted benzoic acid is 77.1 mol %.

EXAMPLE 8

Substantially the same procedure as in Example 4 is repeated except that powdery copper is not used. As a result of the analysis of the reaction mixture, it is found that terephthalic acid and isophthalic acid are obtained in yields of 9.7 mol % and 1.2 mol %, respectively, and phthalic acid is not detected. It is also found that the amount of unreacted benzoic acid is 77.0 mol %.

EXAMPLE 9

Substantially the same procedure as in Example 1 is repeated except that 30 ml of an aqueous 30 wt % potassium hydroxide solution is used instead of the aqueous 30 wt % sodium hydroxide solution. As a result of the analysis of the reaction mixture, it is found that terephthalic acid and isophthalic acid are obtained in yields of 17.1 mol % and 10.3 mol %, respectively, and phthalic acid is not detected. It is also found that the amount of unreacted benzoic acid is 72.0 mol %.

EXAMPLE 10

In substantially the same reaction apparatus as employed in Example 1 are placed 0.36 g (3.00 mmol) of benzoic acid, 0.05 g (0.80 mmol) of copper bronze (manufactured and sold by Aldrich Chemical Co., Ltd., U.S.A.) and 1.7 g (1.50 mmol) of $\beta$-cyclodextrin. After replacing the air in the flask with a nitrogen gas, 30 ml of an aqueous 30 wt % sodium hydroxide solution is added and agitated well by means of a magnetic stirrer, followed by heating to 60° C. 6.0 ml (62.4 mmol) of carbon tetrachloride is added thereto and a reaction is allowed to proceed for 7 hours. Then, the obtained mixture is cooled and the, neutralized and acidified to pH 4 with hydrochloric acid, to thereby terminate the reaction. An aqueous sodium hydrogencarbonate solution is added to the reaction mixture to thereby adjust the pH value to 8 and stirred for 3 hours to thereby dissolve the remaining starting material and the reaction product therein. The resultant solution is subjected to filtration. The obtained filtrate is qualitatively and quantitatively analyzed by liquid chromatography. As a result of the analysis, it is found that terephthalic acid and isophthalic acid are obtained in yields of 63.2 mol % and 12.6 mol %, respectively, and phthalic acid is not detected. It is also found that the amount of unreacted benzoic acid is 17.4 mol %.

EXAMPLE 11

Substantially the same procedure as in Example 10 is repeated except that 15 ml (156 mmol) of carbon tetrachloride is used instead of 6.0 ml (62.4 mmol) of carbon tetrachloride. As a result of the analysis of the reaction mixture, it is found that terephthalic acid and isophthalic acid are obtained in yields of 73.8 mol % and 14.3 mol %, respectively, and phthalic acid is not detected. It is also found that the amount of unreacted benzoic acid is 11.9 mol %.

EXAMPLE 12

Substantially the same procedure as in Example 11 is repeated except that 0.02 g (0.31 mmol) of copper bronze is used instead of 0.05 g (0.80 mmol) of copper bronze. As a result of the analysis of the reaction mixture, it is found that terephthalic acid and isophthalic acid are obtained in yields of 74.4 mol % and 11.8 mol %, respectively, and phthalic acid is not detected. It is also found that the amount of unreacted benzoic acid is 13.8 mol %.

EXAMPLE 13

In substantially the same reaction apparatus as employed in Example 1 are placed 0.60 g (3.00 mmol) of 4-biphenylcarboxylic acid (first class grade reagent, manufactured and sold by Nacalai Tesque, Japan), 0.05 g (0.80 mmol) of powdery copper and 3.4 g (3.00 mmol) of $\beta$-cyclodextrin. After replacing the air in the flask with a nitrogen gas, 30 ml of an aqueous 30 wt % sodium hydroxide solution is added and agitated well by means of a magnetic stirrer, followed by heating to 60° C. 0.9 ml (9.55 mmol) of carbon tetrachloride is added thereto and a reaction is allowed to proceed for 7 hours. Then, the obtained mixture is cooled and acidifield to pH 2 with hydrochloric acid, to thereby terminate the reaction. The reaction mixture is subjected to filtration. The obtained filtrate is diluted with water to 200 ml. 8.5 g of sodium nitrate (special grade reagent, manufactured and sold by Kanto Chemical Co., Ltd., Japan) and 0.6 g of boric acid (special grade reagent, manufactured and sold by Kanto Chemical Co., Ltd., Japan) are added to the diluted filtrate and the pH value thereof is adjusted to 9.8 with an aqueous 1N sodium hydroxide solution (manufactured and sold by Kanto Chemical Co., Ltd., Japan). Further, to the resultant solution is added 50 ml of acetonitrile, and stirred for 3 hours, followed by filtration. The resultant filtrate is qualitatively and quantitatively analyzed by liquid chromatography. On the other hand, to the filter cake of the first-conducted filtration is added 200 ml of the same developing solution as described hereinabove, which contains 0.5M sodium nitrate, 0.05M boric acid (pH 9.8) and 25 vol % acetonitrile and then, the mixture is stirred for 3 hours, followed by filtration. The filtrate is qualitatively and quantitatively analyzed by liquid chromatography. As a result of the analysis, it is found that 4,4'-biphenyldicarboxylic acid is obtained in a yield of 24.9 mol %. It is also found that the amount of unreacted 4-biphenylcarboxylic acid is 38.2 mol %.

EXAMPLE 14

Substantially the same procedure as in Example 13 is repeated except that 1.7 g (1.50 mmol) of β-cyclodextrin is used instead of 3.4 g (3.00 mmol) of β-cyclodextrin. As a result of the analysis of the reaction mixture, it is found that 4,4'-biphenyldicarboxylic acid is obtained in a yield of 19.1 mol %. It is also found that the amount of unreacted 4-biphenylcarboxylic acid is 68.7 mol %.

COMPARATIVE EXAMPLE 4

Substantially the same procedure as in Example 13 is repeated except that β-cyclodextrin is not used. As a result of the analysis of the reaction mixture, it is found that the reaction has substantially not proceeded.

EXAMPLE 15

Substantially the same procedure as in Example 13 is repeated except that 6.0 ml (62.4 mmol) of carbon tetrachloride is used instead of 0.9 ml (9.55 mmol) of carbon tetrachloride. As a result of the analysis of the reaction mixture, it is found that 4,4'-biphenyldicarboxylic acid is obtained in a yield of 28.9 mol %. It is also found that the amount of unreacted 4-biphenylcarboxylic acid is 51.6 mol %.

EXAMPLE 16

Substantially the same procedure as in Example 13 is repeated except that 12.0 ml (125 mmol) of carbon tetrachloride is used instead of 0.9 ml (9.55 mmol) of carbon tetrachloride. As a result of the analysis of the reaction mixture, it is found that 4,4'-biphenyldicarboxylic acid is obtained in a yield of 33.4 mol %. It is also found that the amount of unreacted 4-biphenylcarboxylic acid is 56.3 mol %.

EXAMPLE 17

In substantially the same reaction apparatus as employed in Example 1 are placed 0.60 g (3.00 mmol) of 4-biphenylcarboxylic acid (manufactured and sold by Nacalai Tesque, Japan), 0.05 g (0.80 mmol) of copper bronze and 3.4 g (3.00 mmol) of β-cyclodextrin. After replacing the air in the flask with a nitrogen gas, 30 ml of an aqueous 30 wt % sodium hydroxide solution is added and agitated well by means of a magnetic stirrer, followed by heating to 60° C. 12.0 ml (125 mmol) of carbon tetrachloride is added thereto and a reaction is allowed to proceed for 7 hours. Then, the resultant reaction mixture is cooled and then, neutralized and acidified to pH 5 with hydrochloric acid, to thereby terminate the reaction. The resultant reaction mixture is diluted with water to 200 ml. To the diluted reaction mixture are added 8.5 g of sodium nitrate (special grade reagent, manufactured and sold by Kanto Chemical Co., Ltd., Japan), and 0.6 g of boric acid (special grade reagent, manufactured and sold by Kanto Chemical Co., Ltd., Japan), and the pH value of the resultant mixture is adjusted to 9.8 with an aqueous 1N sodium hydroxide solution. Further, 50 ml of acetonitrile is added thereto and stirred for 3 hours. The resultant mixture is subjected to filtration. The resultant filtrate is qualitatively and quantitatively analyzed by liquid chromatography. As a result of the analysis, it is found that 4,4'-biphenyldicarboxylic acid is obtained in a yield of 64.9 mol %. It is also found that the amount of unreacted 4-biphenylcarboxylic acid is 30.5 mol %.

EXAMPLE 18

In substantially the same reaction apparatus as employed in Example 1 are placed 0.52 g (3.00 mmol) of 2-naphthalenecarboxylic acid (special grade reagent, Nacalai Tesque, Japan), 0.05 g (0.80 mmol) of powdery copper and 3.4 g (3.00 mmol) of β-cyclodextrin. After replacing the air in the flask with a nitrogen gas, 30 ml of an aqueous 30 wt % sodium hydroxide solution is added, and agitated well by means of a magnetic stirrer, followed by heating to 60° C. 0.9 ml (9.55 mmol) of carbon tetrachloride is added thereto and a reaction is allowed to proceed for 7 hours. Then, the resultant reaction mixture is cooled and then, neutralized and acidified to pH 5 with hydrochloric acid, to thereby terminate the reaction. A qualitative analysis of the reaction mixture is carried out in substantially the same manner as in Example 17. As a result, it is found that 2,6-naphthalenedicarboxylic acid is obtained in a yield of 39.0 mol %. It is also found that the amount of unreacted 2-naphthalenecarboxylic acid is 28.2 mol %.

EXAMPLE 19

Substantially the same procedure as in Example 18 is repeated except that 1.7 g (1.50 mmol) of β-cyclodextrin is used instead of 3.4 g (3.00 mmol) of β-cyclodextrin. As a result of the analysis of the reaction mixture, it is found that 2,6-naphthalenedicarboxylic acid is obtained in a yield of 24.4 mol %. It is also found that the amount of unreacted 2-naphthalenecarboxylic acid is 59.3 mol %.

COMPARATIVE EXAMPLE 5

Substantially the same procedure as in Example 18 is repeated except that β-cyclodextrin is not used. As a result of the analysis of the reaction mixture, it is found that the reaction has substantially not proceeded.

EXAMPLE 20

Substantially the same procedure as in Example 18 is repeated except that 0.05 g (0.80 mmol) of copper bronze is used instead of powdery copper. As a result of the analysis of the reaction mixture, it is found that 2,6-naphthalenedicarboxylic acid is obtained in a yield of 44.5 mol %. It is also found that the amount of unreacted 2-naphthalenecarboxylic acid is 27.7 mol %.

EXAMPLE 21

Substantially the same procedure as in Example 18 is repeated except that 0.02 g (0.31 mmol) of copper bronze is used instead of powdery copper. As a result of the analysis of the reaction mixture, it is found that 2,6-naphthalenedicarboxylic acid is obtained in a yield of 47.1 mol %. It is also found that the amount of unreacted 2-naphthalenecarboxylic acid is 27.3 mol %.

EXAMPLE 22

Substantially the same procedure as in Example 4 is repeated except that 0.41 g (3.01 mmol) of orthomethylbenzoic acid is used instead of benzoic acid. As a result of the analysis of the reaction mixture, it is found that only methylterephthalic acid is obtained in a yield of 3.9 mol %. It is also found that the amount of unreacted ortho-methylbenzoic acid is 36.2 mol %.

EXAMPLE 23

Substantially the same procedure as in Example 22 is repeated except that 0.05 g (0.80 mmol) of copper bronze is used instead of powdery copper. As a result of the analysis of the reaction mixture, it is found that only methylterephthalic acid is obtained in a yield of 5.4 mol %. It is also found that the amount of unreacted ortho-methylbenzoic acid is 44.1 mol %.

EXAMPLE 24

Substantially the same procedure as in Example 4 is repeated except that 0.46 g (3.02 mmol) of orthomethoxybenzoic acid is used instead of benzoic acid. As a result of the analysis of the reaction mixture, it is found that only methoxyterephthalic acid is obtained in a yield of 5.4 mol %. It is also found that the amount of unreacted ortho-methoxybenzoic acid is 94.6 mol %.

EXAMPLE 25

Substantially the same procedure as in Example 11 is repeated except that 0.04 g (0.63 mmol) of copper bronze is used instead of 0.05 g (0.80 mmol) of copper bronze. As a result of the analysis of the reaction mixture, it is found that terephthalic acid and isophthalic acid are obtained in yields of 75.1 mol % and 11.1 mol %, respectively. It is also found that the amount of unreacted benzoic acid is 13.7 mol %.

EXAMPLE 26

Substantially the same procedure as in Example 17 is repeated except that 0.08 g (1.26 mmol) of copper bronze is used instead of 0.05 g (0.80 mmol) of copper bronze. As a result of the analysis of the reaction mixture, it is found that 4,4'-biphenyldicarboxylic acid is obtained in a yield of 69.0 mol %. It is also found that the amount of unreacted 4-biphenylcarboxylic acid is 20.0 mol %.

EXAMPLE 27

Substantially the same procedure as in Example 21 is repeated except that 1.5 ml (15.6 mmol) of carbon tetrachloride is used instead of 0.9 ml (9.55 mmol) carbon tetrachloride. As a result of the analysis of the reaction mixture, it is found that 2,6-naphthalenedicarboxylic acid, 2,7-naphthalenedicarboxylic acid and 1,6-naphthalenedicarboxylic acid are obtained in yields of 58.4 mol %, 10.0 mol % and 2.4 mol %, respectively, and unreacted 2-naphthalenecarboxylic acid is not detected.

EXAMPLE 28

Substantially the same procedure as in Example 27 is repeated except that 6.8 g (6.00 mmol) of $\beta$-cyclodextrin is used instead of 3.4 g (3.00 mmol) of $\beta$-cyclodextrin. As a result of the analysis of the reaction mixture, it is found that 2,6-naphthalenedicarboxylic acid, 2,7-naphthalenedicarboxylic acid and 1,6-naphthalenedicarboxylic acid are obtained in yields of 61.2 mol %, 8.8 mol % and 2.6 mol %, respectively, and unreacted 2-naphthalenecarboxylic acid is not detected.

EXAMPLE 29

In substantially the same reaction apparatus as employed in Example 1 are placed 0.52 g (3.00 mmol) of 2-naphthalenecarboxylic acid (special grade reagent, Nacalai Tesque, Japan), 0.02 g (0.31 mmol) of copper bronze and 6.8 g (6.00 mmol) of $\beta$-cyclodextrin. After replacing the air in the flask with a nitrogen gas, 30 ml of an aqueous 30 wt % sodium hydroxide solution is added and agitated well by means of a magnetic stirrer, followed by heating to 60° C. 0.06 ml (0.62 mmol) of carbon tetrachloride is added to the mixture at the time of initiation of the reaction and the reaction is allowed to proceed for 8 hours while adding 0.06 ml (0.62 mmol) of carbon tetrachloride to the reaction system every 15 minutes. Then, the resultant reaction mixture is cooled and then, neutralized and acidified to pH 5 with hydrochloric acid, to thereby terminate the reaction. Analysis for quantitative determination of the reaction mixture is carried out in substantially the same manner as in Example 17. As a result of the analysis, it is found that 2,6-naphthalene-dicarbosyl-ic acid, 2,7-naphthalenedicarboxylic acid and 1,6-naphthalenedicarboxylic acid are obtained in yields of 67.4 mol %, 10.6 mol % and 2.4 mol %, respectively, and unreacted 2-naphthalenecarboxylic acid is not detected.

EXAMPLE 30

Substantially the same procedure as in Example 23 is repeated except that 15 ml (156 mmol) of carbon tetrachloride and 3.4 g (3.00 mmol) of $\beta$-cyclodextrin are used instead of 6.0 ml (62.4 mmol) of carbon tetrachloride and 1.7 g (1.50 mmol) of $\beta$-cyclodextrin, respectively. As a result of the analysis of the reaction mixture, it is found that only methylterephthalic acid is obtained in a yield of 6.2 mol %. It is also found that the amount of unreacted ortho-methyl-benzoic acid is 37.0 mol %.

EXAMPLE 31

Substantially the same procedure as in Example 30 is repeated except that 0.41 g (3.00 mmol) of metamethylbenzoic acid (special grade reagent, manufactured and sold by Tokyo Kasei Co., Ltd., Japan) is used instead of ortho-methylbenzoic acid. As a result of the analysis of the reaction mixture, it is found that only methylterephthalic acid is obtained in a yield of 1.2 mol %. It is also found that the amount of unreacted meta-methylbenzoic acid is 65.5 mol %.

EXAMPLE 32

Substantially the same procedure as in Example 11 is repeated except that 0.47 g (3.00 mmol) of ortho-chlorobenzoic acid (special grade reagent, manufactured and sold by Nacalai Tesque, Japan) is used instead of benzoic acid. As a result of the analysis of the reaction mixture, it is found that chloroterephthalic acid and 6-chloroisophthalic acid are obtained in yields of 5.8 mol % and 3.2 mol %, respectively. It is also found that the amount of unreacted ortho-chlorobenzoic acid is 90.2 mol %.

EXAMPLE 33

Substantially the same procedure as in Example 11 is repeated except that 0.50 g (3.00 mmol) of orthonitrobenzoic acid (special grade reagent, manufactured and sold by Tokyo Kasei Co., Ltd., Japan) is used instead of benzoic acid, and 0.9 ml (9.55 mmol) of carbon tetrachloride is used instead of 15.0 ml (156 mmol) of carbon tetrachloride. As a result of the analysis of the reaction mixture, it is found that nitroterephthalic acid and 3-nitrophthalic acid are obtained in yields of 2.2 mol % and 0.7 mol %, respectively. It is also found that the amount of unreacted ortho-nitrobenzoic acid is 41.0 mol %.

EXAMPLE 34

Substantially the same procedure as in Example 11 is repeated except that 0.50 g (3.00 mmol) of meta-nitrobenzoic acid (special grade reagent, manufactured and sold by Tokyo Kasei Co., Ltd., Japan) is used instead of benzoic acid, and a reaction is conducted for 5 minutes instead of 7 hours. As a result of the analysis of the reaction mixture, it is found that only 5-nitroisophthalic acid is obtained in a yield of 2.5 mol %. It is also found that the amount of unreacted meta-nitrobenzoic acid is 43.3 mol %.

EXAMPLE 35

Substantially the same procedure as in Example 11 is repeated except that 0.68 g (3.00 mmol) of 4-benzoylbenzoic acid (special grade reagent, manufactured and sold by Wako Pure Chemical Industries Ltd., Japan) is used instead of benzoic acid, and 3.4 g (3.00 mmol) of $\beta$-cyclodextrin is used instead of 1.7 g (1.5 mmol) of $\beta$-cyclodextrin. As a result of the analysis of the reaction mixture, it is found that only 4-(4'-carboxybenzoyl)benzoic acid is obtained in a yield of 11.7 mol %. It is also found that the amount of unreacted 4-benzoylbenzoic acid is 67.9 mol %.

EXAMPLE 36

Substantially the same procedure as in Example 11 is repeated except that 0.64 g (3.00 mmol) of 4-phenoxybenzoic acid is used instead of benzoic acid, and 3.4 g (3.00 mmol) of $\beta$-cyclodextrin is used instead of 1.7 g (1.5 mmol) of $\beta$-cyclodextrin. As a result of the analysis of the reaction mixture, it is found that only 4-4'-dicarboxy-diphenyl ether is obtained in a yield of 2.0 mol %. It is also found that the amount of unreacted 4-phenoxybenzoic acid is 84.4 mol %. The 4-phenoxybenzoic acid used in the above is synthesized using 4-phenoxyacetophenone (manufactured and sold by Aldrich Chemical Co., Ltd., U.S.A.), potassium hypochlorite (first class grade reagent, manufactured and sold by Kanto Chemical Co., Ltd., Japan), sodium hydrogensulfite (special grade reagent, manufactured and sold by Nacalai Tesque, Japan) and chloroform (special grade reagent, manufactured and sold by Nacalai Tesque, Japan) and purified according to the method described in Journal of Polymer Science: Polymer Chemistry Edition 23, pp. 2205-2223 (1985), written by Marta I. Litter and C.S. Marvel.

What is claimed is:

1. A process for introducing a carboxyl group to an aromatic carboxylic acid or a derivative thereof, which comprises: reacting an aromatic carboxylic acid or a derivative thereof represented by the following formula:

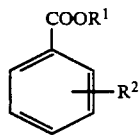

(1)

wherein:
$R^1$ is a hydrogen atom, an alkyl group or an alkali metal, and
$R^2$ is a hydrogen atom, an alkyl group, an alkoxyl group, a carboxyl group, a nitro group or a halogen atom, bonded to the ortho- or meta-position relative to COOR$^1$, with a carbon tetrahalide in the presence of a cyclodextrin and an alkali metal hydroxide, thereby introducing a carboxyl group to said aromatic carboxylic acid or said derivative thereof in substitution for a hydrogen atom which is bonded to an aromatic ring of said aromatic carboxylic acid or said derivative thereof.

2. A process for introducing a carboxyl group to an aromatic carboxylic acid or a derivative thereof, which comprises: reacting an aromatic carboxylic acid or a derivative thereof represented by the following formula:

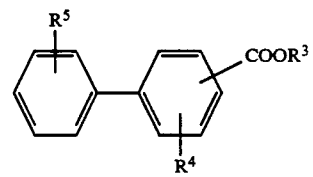

(2)

wherein:
$R^3$ is a hydrogen atom, an alkyl group or an alkali metal,
$R^4$ is a hydrogen atom, an alkyl group, an alkoxyl group, a carboxyl group, a nitro group, an amino group or a halogen atom,
COOR$^3$ is bonded to the 2-, 3- or 4-position, in which,
$R^4$ is bonded to the 3-, 4-, 5- or 6-position when COOR$^3$ is bonded to the 2-position, bonded to the 2-, 4-, 5- or 6-position when COOR$^3$ is bonded to the 3-position, and bonded to the 2- or 3-position when COOR$^3$ is bonded to the 4-position, and
$R^5$ is a hydrogen atom, a hydroxyl group, an alkyl group, an alkoxyl group, a carboxyl group, a nitro group, an amino group or a halogen atom, bonded to the 2'-, 3'-, 4'-, 5'- or 6'- position,
with a carbon tetrahalide in the presence of a cyclodextrin and an alkali metal hydroxide, thereby introducing a carboxyl group to said aromatic carboxylic acid or said derivative thereof in substitution for a hydrogen atom which is bonded to an aromatic ring of said aromatic carboxylic acid or said derivative thereof.--

3. A process for introducing a carboxyl group to an aromatic carboxylic acid or a derivative thereof, which comprises: reacting an aromatic carboxylic acid or a derivative thereof represented by the following formula:

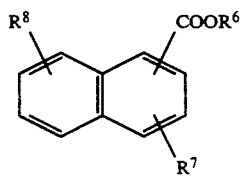

(3)

wherein:
$R^6$ is a hydrogen atom, an alkyl group or an alkali metal,

R⁷ is a hydrogen atom, a hydroxyl group, an alkyl group, an alkoxyl group, a carboxyl group, a nitro group, an amino group or a halogen atom, COOR⁶ is bonded to the 1- or 2-position, in which, R⁷ is bonded to the 2-, 3-, or 4-position when COOR⁶ is bonded to the 1-position, and bonded to the 1-, 3- or 4-position when COOR⁶ is bonded to the 2-position, and R⁸ is a hydrogen atom, a hydroxyl group, an alkyl group, an alkoxyl group, a carboxyl group, a nitro group, an amino group or a halogen atom, bonded to the 5-, 6-, 7-, or 8-position, with a carbon tetrahalide in the presence of a cyclodextrin and an alkali metal hydroxide, thereby introducing a carboxyl group to said aromatic carboxylic acid or said derivative thereof in substitution for a hydrogen atom which is bonded to an aromatic ring of said aromatic carboxylic acid or said derivative thereof.

4. The process according to claim 3, wherein said reaction is performed in the presence of a reaction medium.

5. The process according to claim 3, wherein said carbon tetrahalide is used in an amount of from 1 to 100 moles per mole of said aromatic carboxylic acid or said derivative thereof.

6. The process according to claim 3, wherein said cyclodextrin is used in an amount of from 0.01 to 5 moles per mole of said aromatic carboxylic acid or said derivative thereof.

7. The process according to claim 3, wherein said alkali metal hydroxide is used in an amount of from 3 to 130 moles per mole of said aromatic carboxylic acid or said derivative thereof.

8. The process according to claim 4, wherein said alkali metal hydroxide is used in the form of a solution thereof in said reaction medium in a concentration of from 1 to 50% by weight.

9. The process according to any one of claims 3 to 8, wherein said alkali metal hydroxide is sodium hydroxide or potassium hydroxide.

10. The process according to any one of claims 3 to 8, wherein said carbon tetrahalide is carbon tetrachloride or carbon tetrabromide.

11. The process according to any one of claims 3 to 8, wherein said reaction is carried out in the presence of a copper catalyst.

12. The process according to any one of claims 3 to 8, wherein said cyclodextrin is selected from the group consisting of β-cyclodextrin, γ-cyclodextrin, a modified cyclodextrin and a solid, fixed cyclodextrin.

13. A process for introducing a carboxyl group to an aromatic carboxylic acid or a derivative thereof, which comprises: reacting an aromatic carboxylic acid or a derivative thereof represented by the following formula:

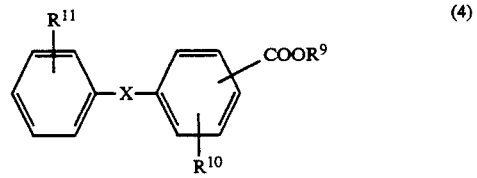

(4)

wherein:

R⁹ is a hydrogen atom, an alkyl group or an alkali metal,

R¹⁰ is a hydrogen atom, a hydroxyl group, an alkyl group, an alkoxyl group, a carboxyl group, a nitro group, an amino group or a halogen atom, COOR⁹ is bonded to the 2-, 3- or 4-position, in which, R¹⁰ is bonded to the 3-, 4-, 5- or 6-position when COOR⁹ is bonded to the 2-position, bonded to the 2-, 4-, 5- or 6-position when COOR⁹ is bonded to the 3-position, and bonded to the 2-or 3-position when COOR⁹ is bonded to the 4-position, R¹¹ is a hydrogen atom, a hydroxyl group, an alkyl group, an alkoxyl group, a carboxyl group, a nitro group, an amino group or a halogen atom, bonded to the 2'-, 3'-, 4'-, 5'- or 6'-position, and X is —O—, —CH₂—, —C(CH₃)₂—, —CH=CH—, —(C=O)—, —NH—, —N=N—, —S— or —SO₂—, with a carbon tetrahalide in the presence of a cyclodextrin and an alkali metal hydroxide, thereby introducing a carboxyl group to said aromatic carboxylic acid or said derivative thereof in substitution for a hydrogen atom which is bonded to an aromatic ring of said aromatic carboxylic acid or said derivative thereof.

* * * * *